(12) United States Patent
Izu et al.

(10) Patent No.: US 12,263,265 B2
(45) Date of Patent: Apr. 1, 2025

(54) HANDRAIL DISINFECTION SYSTEM FOR VEHICLE WITH HANDRAIL

(71) Applicant: TOYOTA JIDOSHA KABUSHIKI KAISHA, Toyota Aichi-ken (JP)

(72) Inventors: Hiroki Izu, Nagoya (JP); Daisuke Sato, Susono (JP); Daisuke Ishii, Sunto-gun. Shizuoka-ken (JP); Hiroki Morita, Hiratsuka (JP); Kei Sato, Toyota (JP); Masaki Nanahara, Toyota (JP); Kazumi Serizawa, Toyota (JP); Hironobu Tanaka, Tokyo-to (JP); Shunsuke Mogi, Hachioji (JP); Takashi Hayashi, Nagoya (JP); Akihiro Kusumoto, Susono (JP)

(73) Assignee: TOYOTA JIDOSHA KABUSHIKI KAISHA, Toyota (JP)

(*) Notice: Subject to any disclaimer, the term of this patent is extended or adjusted under 35 U.S.C. 154(b) by 850 days.

(21) Appl. No.: 17/493,008

(22) Filed: Oct. 4, 2021

(65) Prior Publication Data
US 2022/0105216 A1   Apr. 7, 2022

(30) Foreign Application Priority Data
Oct. 6, 2020   (JP) ................... 2020-169400

(51) Int. Cl.
*A61L 2/18* (2006.01)
*A61L 2/24* (2006.01)

(52) U.S. Cl.
CPC .................. *A61L 2/18* (2013.01); *A61L 2/24* (2013.01); *A61L 2202/14* (2013.01); *A61L 2202/15* (2013.01)

(58) Field of Classification Search
CPC .......... A61L 2/18; A61L 2/24; A61L 2202/14; A61L 2202/15; B60N 2/75; B60N 2/90
See application file for complete search history.

(56) References Cited

U.S. PATENT DOCUMENTS

| | | | | |
|---|---|---|---|---|
| 5,507,310 A | * | 4/1996 | Sordello | E03B 7/12 137/563 |
| 10,836,291 B2 | * | 11/2020 | Line | B08B 3/08 |
| 2016/0158396 A1 | * | 6/2016 | Beckman | F24D 17/0078 141/2 |

FOREIGN PATENT DOCUMENTS

| | | | | |
|---|---|---|---|---|
| CN | 101716356 A | | 6/2010 | |
| DE | 102009030534 A1 | * | 12/2010 | ......... F24D 17/0073 |

(Continued)

OTHER PUBLICATIONS

English Translation of DE-102009030534-A1 (Year: 2010).*

(Continued)

*Primary Examiner* — Sean E Conley
*Assistant Examiner* — Aham Lee
(74) *Attorney, Agent, or Firm* — Dinsmore & Shohl LLP

(57) ABSTRACT

A handrail disinfection system for vehicle with handrail is mounted on a vehicle having handrail for grasping by an occupant. The handrail disinfection system includes a tank to store disinfectant solution, an exudation part provided on the handrail, an actuator for exuding the disinfectant solution stored in the tank from the exudation part, and a controller for controlling the actuator. At least one processor included in the controller executes upon execution of at least one program, performing a disinfecting process in which the actuator is controlled to exude the disinfectant solution from the exudation part to a surface of the handrail when a predetermined execution condition is satisfied.

10 Claims, 16 Drawing Sheets

(56) References Cited

FOREIGN PATENT DOCUMENTS

| | | | | | |
|---|---|---|---|---|---|
| JP | 2008-237845 | A | | 10/2008 | |
| JP | 2011245305 | A | * | 12/2011 | ............... A61L 2/10 |
| JP | 2020-045027 | A | | 3/2020 | |
| KR | 20110030181 | A | * | 3/2011 | ............. G06Q 50/26 |
| KR | 20200098792 | A | * | 8/2020 | |

OTHER PUBLICATIONS

English Translation of JP-2011245305-A (Year: 2011).*
English Translation of KR-20110030181-A (Year: 2011).*
English Translation of KR 20200098792 A (Year: 2020).*
English translation of Lee (Year: 2020).*

* cited by examiner

HANDRAIL DISINFECTION SYSTEM FOR VEHICLE WITH HANDRAIL

CROSS-REFERENCE TO RELATED APPLICATION

The present application claims priority under 35 U.S.C. § 119 to Japanese Patent Application No. 2020-169400, filed Oct. 6, 2020, the contents of which application are incorporated herein by reference in their entirety.

BACKGROUND

Field

The present disclosure relates to a handrail disinfection system for vehicles with handrails, and more particularly, to a handrail disinfection system for disinfecting a handrail held by an occupant who is standing on board.

Background

Japanese Patent Application Laid-Open No. 2020-045027 discloses a technique related to a sterilization device for sterilizing a hanging leather used by a passenger on trains or buses. In the sterilization device of this technique, sterilization is performed by irradiating ultraviolet rays to the handle of the hanging leather.

SUMMARY

The device disclosed in Japanese Patent Application Laid-Open No. 2020-045027, since using ultraviolet rays for sterilization, a large-scale device is required. It would be advantageous for both the vehicle user (occupant) and the vehicle administrator to be able to automatically disinfect the handrail in a vehicle with handrail without any particular effort.

The present disclosure has been made in view of the above-mentioned problems, and an object thereof is to provide a handrail disinfection system for a handrail vehicle which can disinfect the handrail automated without taking special labor.

In order to solve the above problem, the first disclosure is applied to a handrail disinfection system for vehicle with handrail. The handrail disinfection system includes a tank to store disinfectant solution, an exudation part provided on the handrail, an actuator for exuding the disinfectant solution stored in the tank from the exudation part, and a controller for controlling the actuator. The controller includes at least one memory including at least one program, and at least one processor coupled with the at least one memory. The at least one processor executes upon execution of the at least one program, performing a disinfecting process in which the actuator is controlled to exude the disinfectant solution from the exudation part to a surface of the handrail when a predetermined execution condition is satisfied.

The second disclosure further includes the following features in the first disclosure.

The execution condition is a condition that is satisfied when an elapsed time since a previous execution of the disinfecting process exceeds a predetermined time.

The third disclosure further includes the following features in the first disclosure.

The handrail disinfection system further includes one or more sensors to detect a state of an occupant riding in the vehicle. The at least one memory is configured to store occupant information detected by the one or more sensors. The at least one processor is configured to execute, by executing the at least one program, a getting-off determination process to determine whether the occupant has got off, based on the occupant information. The execution condition is a condition that is satisfied when getting-off of the occupant is determined in the getting-off determination process.

The fourth disclosure further includes the following features in the first disclosure.

The memory is configured to store occupant information detected by the sensor. The at least one memory is configured to store occupant information detected by the one or more sensors. The disinfection exudation part is provided in each of a plurality of areas when the handrail is distinguished into the plurality of areas. The actuator is configured to be capable of exuding the disinfectant solution in each area of the plurality of areas. The at least one processor executes upon execution of the at least one program, executing a disinfection area determination process for determining a disinfection area to be disinfected among the plurality of areas of the handrail based on the occupant information, and executing the disinfecting process by limiting the disinfection area determination process to the disinfection area determined by the disinfection area determination process.

The fifth disclosure further includes the following features in the fourth disclosure.

The disinfection area determination process is configured to determine whether the occupant has got off for each riding area of the riding floor on the basis of the occupant information, and determine an area of the handrail corresponding to a riding area in which the occupant has got off as the disinfection area.

The sixth disclosure further includes the following features in the fourth disclosure.

The disinfection area determination process is configured to determine an area grasped by the occupant among the plurality of areas as the disinfection area based on the occupant information.

The seventh disclose further includes the following features in the fourth disclosure.

The vehicle has a plurality of gateways for occupants to get on and off. The disinfection area determination process is configured to determine the gateways where the occupant has got off from among the plurality of gateways, based on the occupant information, and determine an area corresponding to the gateway where the occupant has got off as the disinfection area.

The eighth disclosure further includes the following features in the fourth disclosure.

The handrail disinfection system further includes a plurality of displays provided in association with each of the plurality of areas. The plurality of displays are configured to be capable of independently displaying a disinfection state of a corresponding one of the plurality of areas. The at least one processor is configured to, by executing the at least one program, display on a corresponding display among the plurality of the display a display indicating that the disinfection area determined by the disinfection area determination process is before disinfection, and to switch to a display indicating that the disinfecting process for the disinfection area has been completed in response to completion of the disinfecting process.

The ninth disclosure further includes the following features in the eighth disclosure.

The plurality of displays includes an illumination lamp provided along each of the plurality of areas. In the illumination lamp, a display indicating that the disinfecting process has not been completed corresponds to lit-state, and a display indicating that the disinfecting process has been completed corresponds to unlit-state.

The tenth disclosure further includes the following features in the first disclosure.

The at least one processor is configured to execute, by executing the at least one program, a notification process for notifying occupants when the disinfecting process is executed.

The eleventh disclosure further includes the following features of the third disclosure.

The at least one memory stores a set vehicle speed in a section to a next pickup location determined based on an operation plan of the vehicle. The at least one processor is configured to increase, by executing the at least one program, amount of disinfectant solution exuded from the disinfection part as the set vehicle speed increases in the disinfecting process.

The twelfth disclosure further includes the following features in the third disclosure.

The at least one memory stores time required to reach a next pickup location determined based on an operation plan of the vehicle. The at least one processor is configured to reduce, by executing the at least one program, amount of the disinfectant solution exuded from the exudation part in the disinfecting process as the time required is shorter.

According to the first disclosure, it is possible to exude the disinfectant solution from the exudation part provided in the handrail of the vehicle when the predetermined execution condition is satisfied. Thereby, it is possible to automatically disinfect the handrail without special labor.

According to the second disclosure, since the disinfecting process is performed when the elapsed time from the previous disinfecting process exceeds the predetermined time, it is possible to disinfect the handrail periodically.

According to the third disclosure, since the disinfecting process is performed when the occupant has got off, it becomes possible for the next occupant to utilize the disinfected handrail.

According to the fourth disclosure, the disinfecting process can be performed by limiting the area to be disinfected among the respective areas when the handrail is distinguished into a plurality of areas. This enables an economical and efficient disinfecting process.

Specifically, according to the fifth disclosure, it is possible to perform an efficient disinfecting process limited to the area of the handrail corresponding to the riding area in which the occupant who has got off the vehicle was riding. According to the sixth disclosure, it is possible to perform an efficient disinfecting process limited to an area grasped by an occupant. Further, according to the seventh disclosure, it is possible to perform an efficient disinfecting process limited to the gateway where the occupant has got off.

According to the eighth disclosure, since the disinfection status of each of the plurality of areas of the handrail can be displayed, the occupant can know the disinfection status of the handrail by area.

Specifically, according to the ninth disclosure, the area before disinfection is displayed in the lit-state, and the area after disinfection is displayed in the unlit state. Thereby, the occupant can clearly recognize that the handrail has been disinfected.

According to the tenth disclosure, when the disinfecting process is performed, the notification is given to the occupant, so that the next occupant can grasp the handrail with peace of mind.

According to the eleventh disclosure, the larger the set vehicle speed to the next pickup location, the greater the amount of exudation of the disinfectant in the disinfecting process. This makes it possible to increase the exuded amount of disinfectant solution in an operating environment where the disinfectant is easily vaporized, thus ensuring reliable disinfection regardless of the operating environment.

According to the twelfth disclosure, the shorter the time until arrival at the next pickup location, the lower the amount of the disinfectant solution exuded in the disinfecting process. This makes it possible to complete the disinfecting process by the time the next occupant gets on.

DETAILED DESCRIPTION

Hereinafter, an embodiment of the present disclosure will be described with reference to the accompanying drawings.

However, it is to be understood that even when the number, quantity, amount, range or other numerical attribute of each element is mentioned in the following description of the embodiment, the present disclosure is not limited to the mentioned numerical attribute unless explicitly described otherwise, or unless the present disclosure is explicitly specified by the numerical attribute theoretically.

1. First Embodiment

1-1. Configuration Example of Stand-Up Type Vehicles

Figure 1:
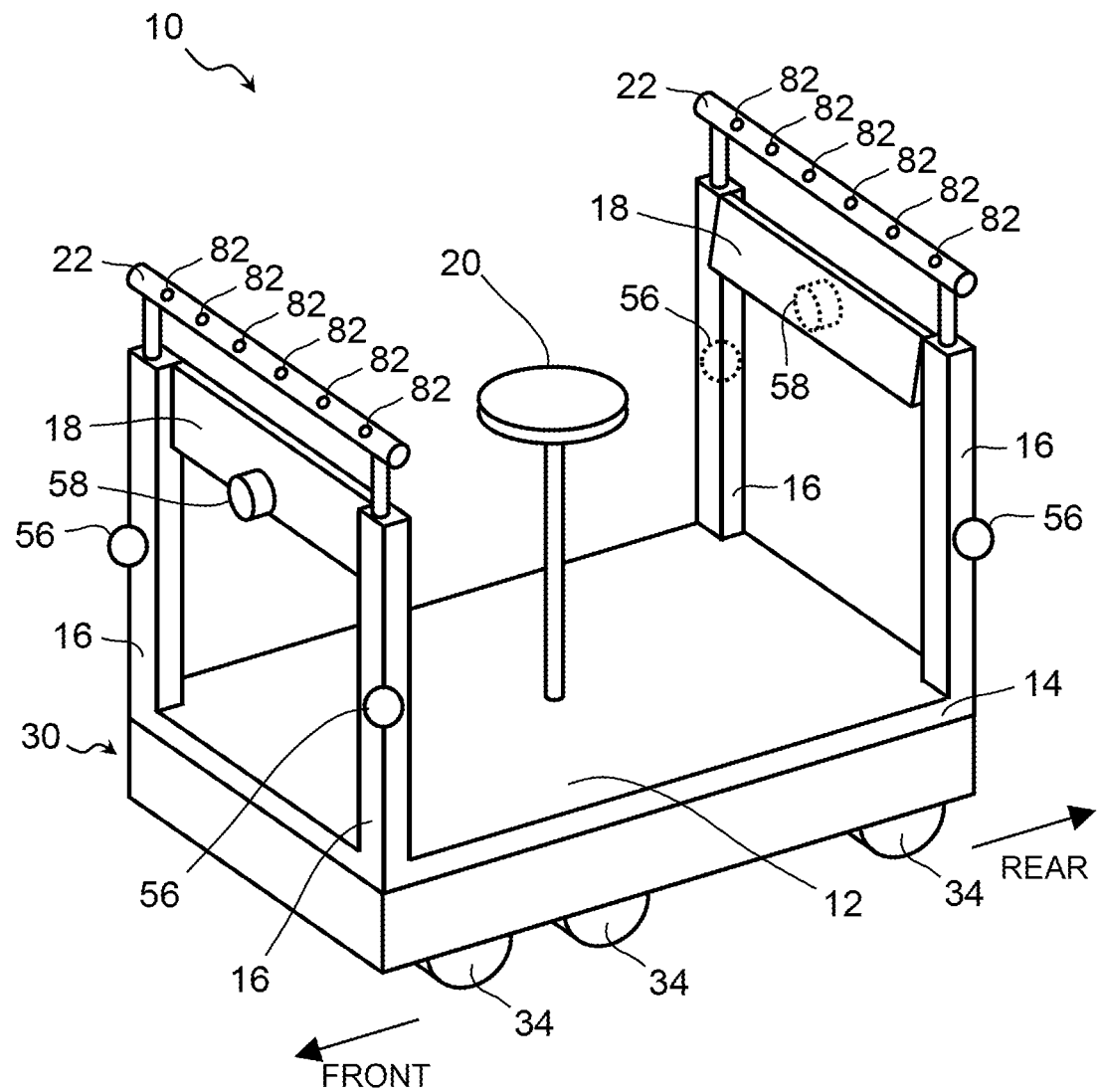
FIG. 1 is a perspective view of a stand-up type vehicle according to a first embodiment.
Figure 2:
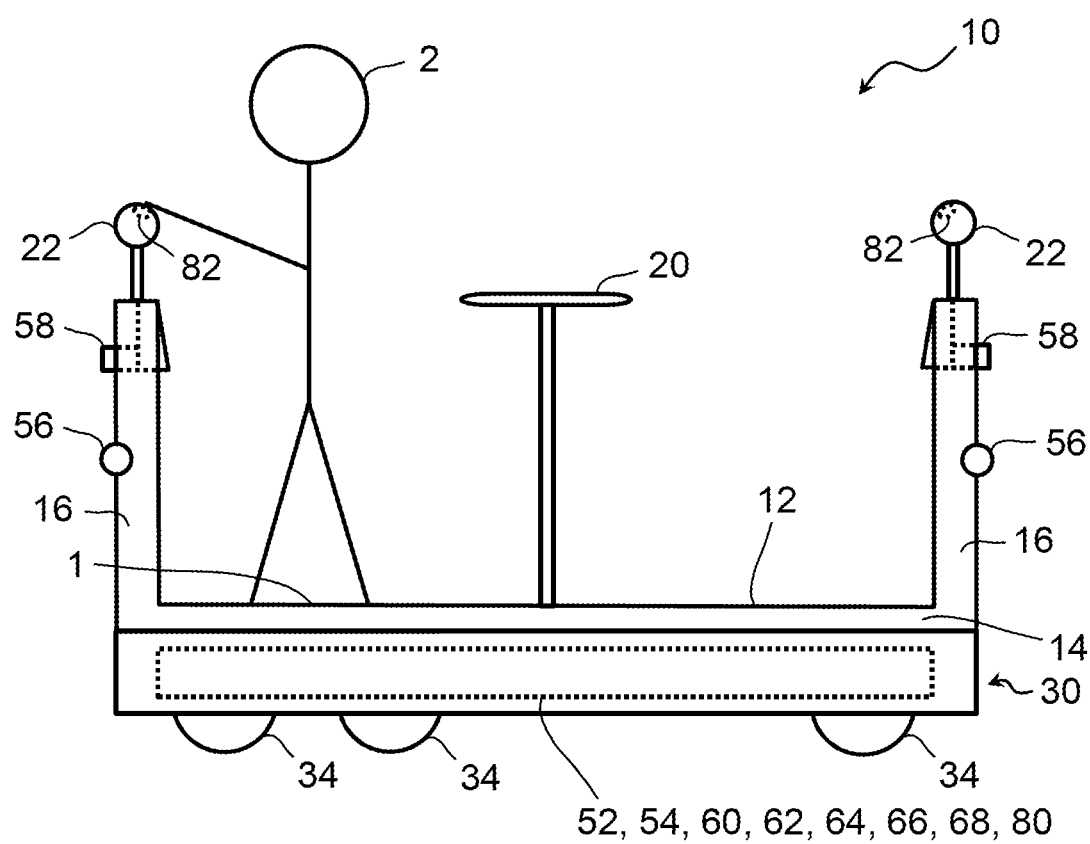
FIG. 2 is a side view of the stand-up type vehicle shown in FIG. 1.
Figure 3:
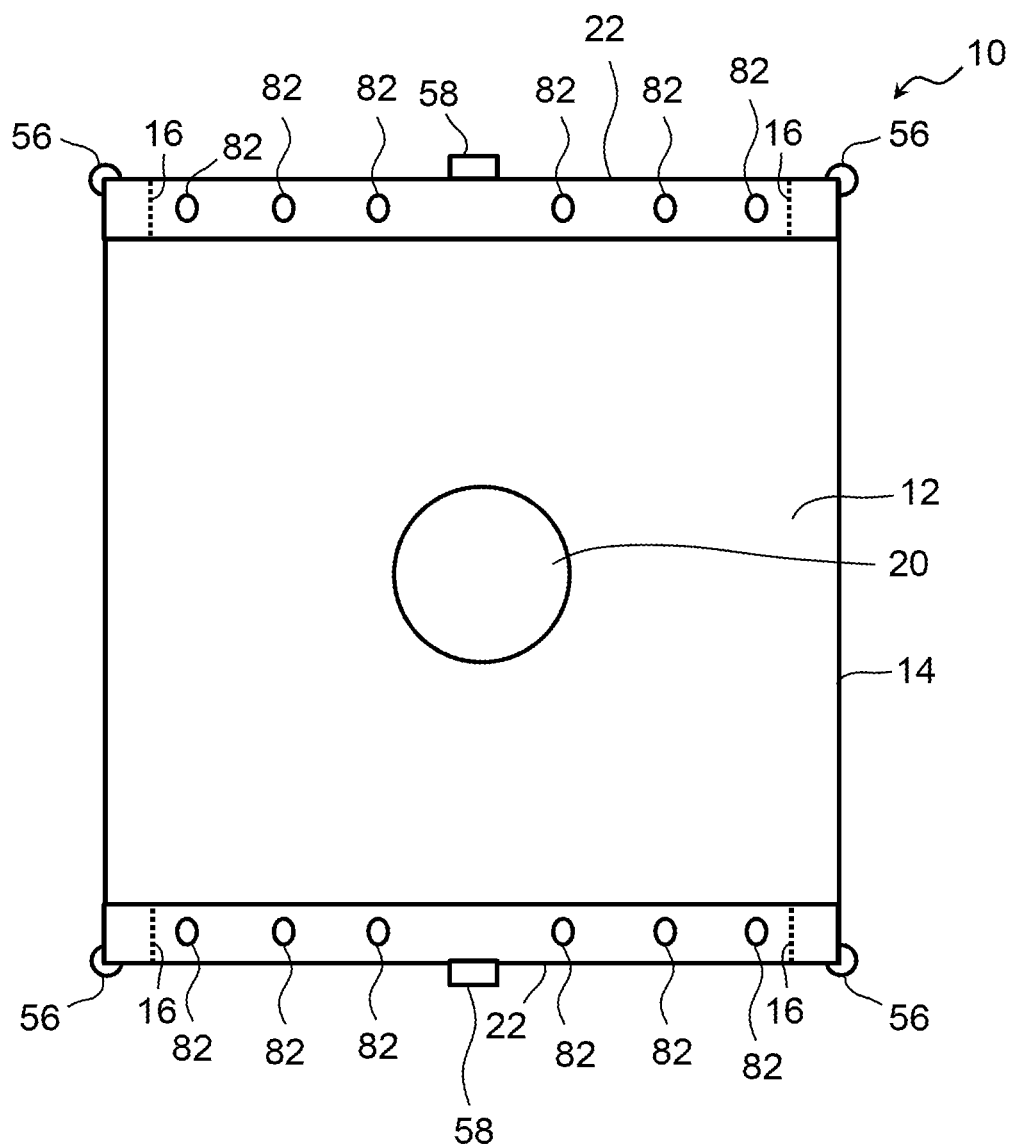
FIG. 3 is a plan view of the stand-up type vehicle shown in FIG. 1.

FIG. 1 is a perspective view of a stand-up type vehicle according to a first embodiment. FIGS. 2 and 3 are a side view and a plan view of the stand-up type vehicle shown in FIG. 1, respectively.

The stand-up type vehicle 10 includes a top plate 14 having a riding floor (deck) 12 on which occupants stand. The top plate 14 forms an upper portion of the vehicle 10. The riding floor 12 is an upper surface of the top plate 14. The stand-up type vehicle 10 is a type of automated traveling vehicle that can be operated unattended. In the following description, the stand-up vehicle 10 is also referred to as an autonomous traveling pallet 10 for moving a person in order to carry a person riding on the top plate 14, and is hereinafter simply referred to as a "pallet 10". Although the riding capacity of such a stand-up vehicle (pallet) is not particularly limited, the riding capacity of the pallet 10 of the present embodiment is, for example, four persons. That is, the pallet 10 is a small vehicle of the stand-up type (e.g., a micro pallet or cart). The pallet 10 is not a vehicle for automated traveling only described below, it may have a function of traveling by the operation of the passenger or the driver.

In the pallet 10, it is possible to freely select the configuration of the riding space located on the riding floor 12 of the top plate 14. An example of the configuration is shown in FIGS. 1 to 3. That is, a support 16 is provided at each of the four corners of the riding floor 12. Each support 16 stands upright from the riding floor 12. The support 16 may be formed integrally with the top plate 14 or may be separate from the top plate 14.

The pallet 10 is provided with a backrest 18 at both its front end and rear end. The backrest 18 is formed so as to connect the tips of the two supports 16 at the front end and the rear end of the pallet 10, respectively. The occupant of the pallet 10 can take a standing state while leaning against the backrest 18 while riding. In addition, a table 20 convenient for the occupant is attached to the central of the riding floor 12.

Furthermore, the pallet 10 in provided with a handrail 22 both its front end and rear end. That is, the pallet 10 is a vehicle with handrails. These handrails 22 are provided for the occupant 2 and other users to grip during the ride. As an example, the handrail 22 is formed above the backrest 18 so as to bridge the tips of the two supports 16 at the front end and the rear end, respectively.

An exudation part 82 is exposed on the surface of the handrail 22. The exudation part 82 is a component of a handrail disinfection system 80 which is a feature of the first embodiment, and is used for exuding disinfectant solution for disinfecting handrails. The detailed structure and execute of the handrail disinfection system 80 will be described in detail later with additional reference to FIGS. 7 to 9.

Furthermore, the pallet 10 is provided with a chassis unit 30 relating to the traveling function together with the top plate 14. The top plate 14 is, for example, a separate body from the upper surface of the chassis unit 30, and is mounted on the chassis unit 30. Alternatively, the top plate 14 may form the upper surface of the chassis unit 30.

Figure 4:
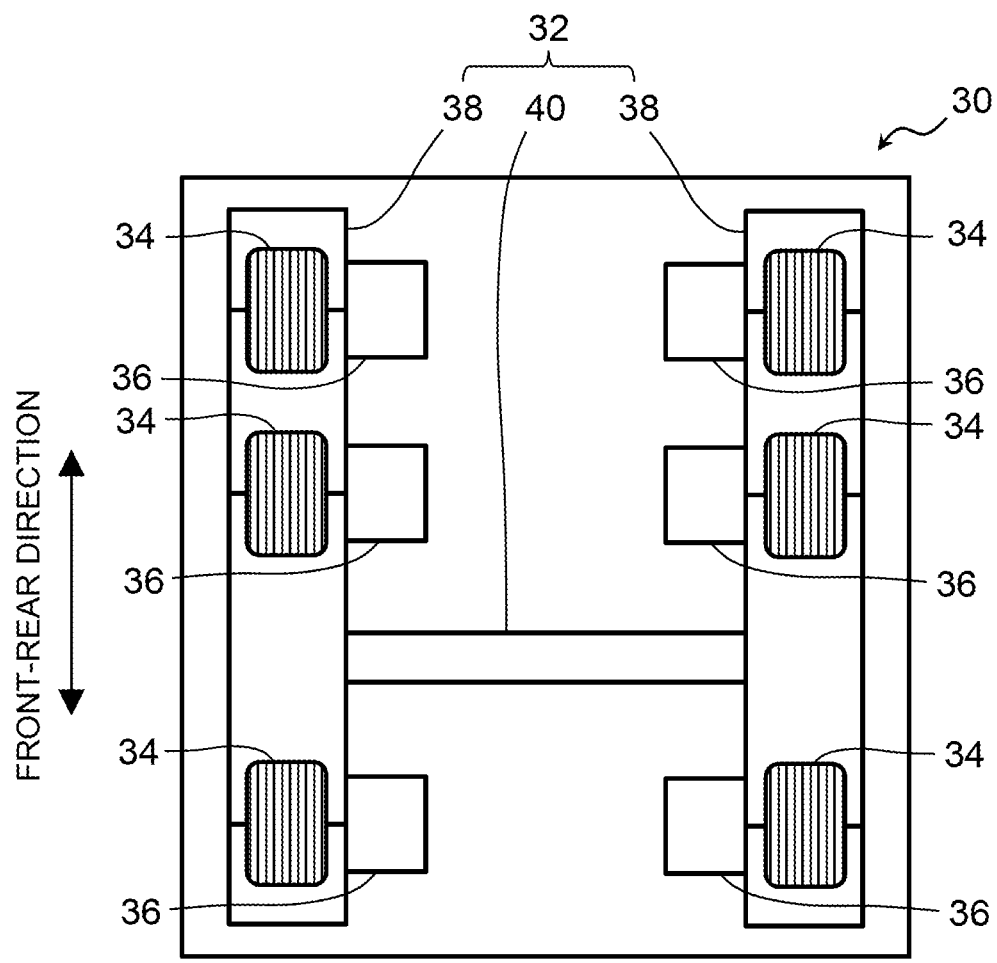
FIG. 4 is a diagram showing a configuration example of a chassis unit shown in FIG. 1.

FIG. 4 is additionally referred to with reference to FIGS. 1 to 3. FIG. 4 is a diagram showing a configuration example of the chassis unit 30 shown in FIG. 1. The chassis unit 30 includes a frame 32, wheels 34, and an electric motor 36. As an example, six wheels 34 are provided. More specifically, three wheels 34 are disposed on each of the left and right sides of the pallet 10 in a bilaterally symmetrical manner. Then, the electric motor 36 is provided for each of the six wheels 34, for example, coaxially.

It should be noted that the number of the wheels 34 is arbitrarily determined in accordance with requirements such as the riding capacity of the pallet 10 and the required driving force thereof. Instead of six, for example, a total of four wheels, i.e., two wheels on the left and two wheels on the right, may be used. Further, the number of the electric motors 36 does not necessarily have to be the same as the number of the wheels 34, and may be changed according to requirements such as the required driving force. The electric motor 36 is an example of a power unit for driving the pallet 10, and another example of the power unit is an internal combustion engine.

FIG. 4 shows a schematic shape of the frame 32. The frame 32 includes a main member 38 extending in the front-rear direction of the pallet 10 on each of the left and right sides of the pallet 10, and a sub-member 40 connecting the two main members 38. Three left wheels 34 and three electric motors 36 for driving them are fixed to the main member 38 on the left of the pallet 10. Similarly, three right wheels 34 and three electric motors 36 for driving them are fixed to the main member 38 on the right of the pallet 10.

Acceleration and deceleration of the pallet 10 is performed by controlling the electric motors 36. Further, the pallet 10 can be braked, for example, by using a regenerative brake realized by the control of the electric motors 36. The pallet 10 may also include a mechanical brake on any wheels 34 for braking.

Moreover, according to the pallet 10 including the above-described chassis unit 30, by providing a difference between the rotational speeds of the three wheels 34 on the left side and the rotational speeds of the three wheels 34 on the right side, the pallet 10 can be turned to the left and right. Further, in the example shown in FIG. 4, each wheel 34 is a wheel having a general structure in which tires are incorporated. Alternatively, in order to increase the degree of freedom of turning of the pallet 10, for example, four wheels 34 located at both ends in the front-rear direction may be replaced by omni-directional movement wheels (so-called, omni-wheels). Alternatively, a steering mechanism, for example, may be used to turn the pallet 10.

In addition, although the pallet 10 of the present embodiment is a wheeled vehicle including wheels 34, the stand-up vehicle (pallet) according to the present disclosure is not limited to this, and may be configured as a tracked vehicle having an infinite track such as a caterpillar.

Figure 5:
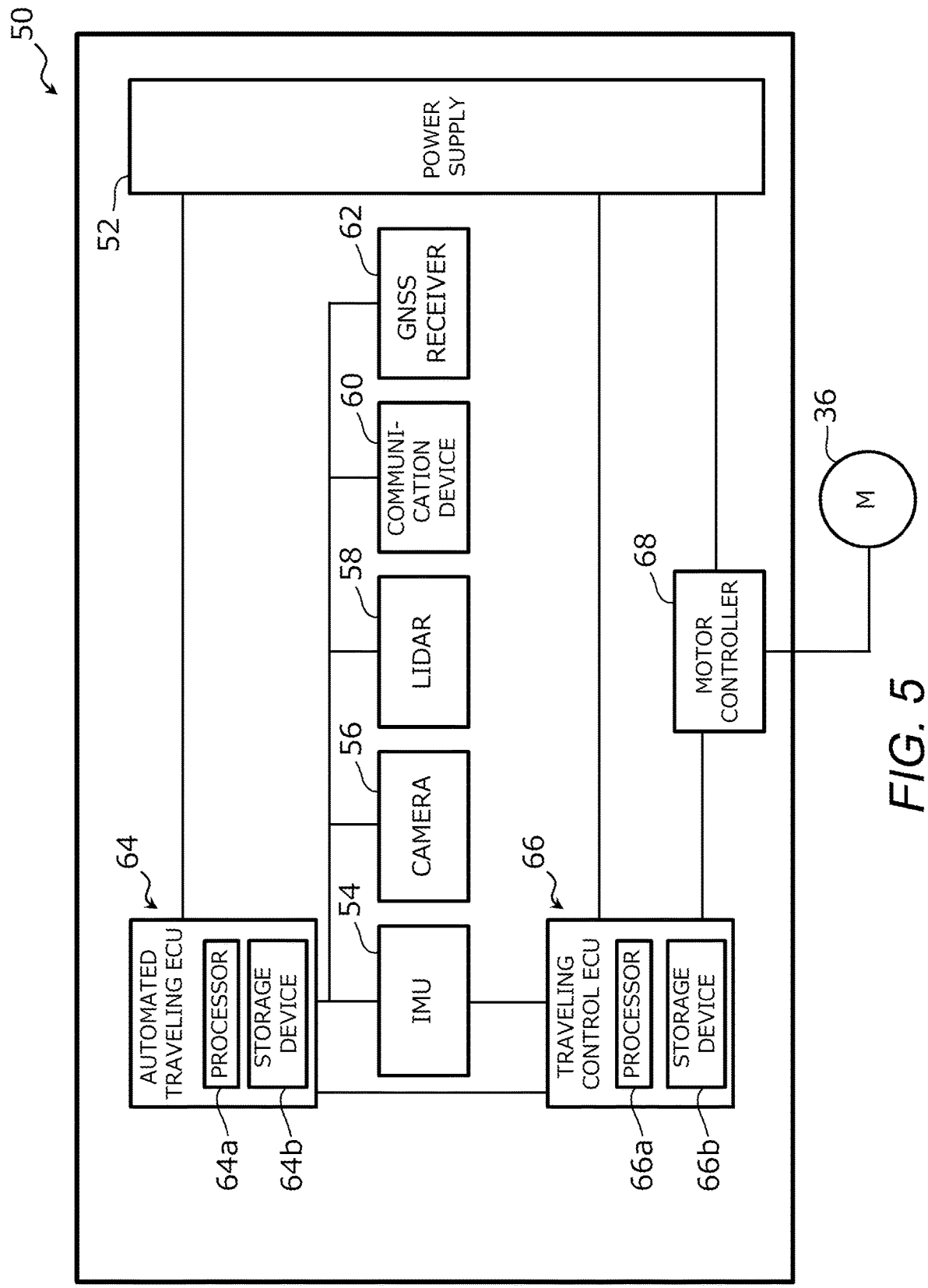
FIG. 5 is a block diagram schematically showing an example of a configuration of a control system mounted on the stand-up type vehicle shown in FIG. 1.

FIG. 5 is a block diagram schematically showing an example of a configuration of a control system 50 mounted on the stand-up type vehicle shown in FIG. 1. The control system 50 for controlling the traveling of the pallet 10 is mounted on the pallet 10. The control system 50 has a function of autonomously traveling the pallet 10.

As shown in FIG. 5, the control system 50 includes a power supply 52, an inertial measurement unit (IMU) 54, a camera 56, a LIDAR (Laser Imaging Detection and Ranging) 58, a communication device 60, a GNSS (Global Navigation Satellite System) receiver 62, an automated traveling ECU (Electronic Control Unit) 64, a traveling control ECU 66, and a motor controller 68. As shown in FIG. 1, the cameras 56 are installed on each of the four supports 16, and the LIDARs 58 are installed on the back surface of each of the two backrests 18. As shown in FIG. 2, the components 52, 54, 60-68 of control system 50 other than the cameras 56 and the LIDARs 58 are disposed between the frame 32 and the top plate 14.

The power supply 52 is typically an externally charged battery. The power supply 52 supplies electric power to each device (the electric motor 36, the control system 50, and a handrail disinfection system 80 described later (e.g., FIG. 7) mounted on the pallet 10. The IMU54 detects angular velocities and accelerations of three axes. Therefore, according to the IMU54, it is possible to acquire various traveling states such as speeds, accelerations, attitudes, and the like of the pallet 10. The IMU 54 transmits the acquired traveling states to the automated traveling ECU 64 and the traveling control ECU 66.

The cameras 56 and the LIDARs 58 are examples of "one or more external sensors" for recognizing the surrounding environment of the pallet 10. The four cameras (outward facing cameras) 56 image the periphery of the pallet 10 (more detail, the right front, left front, right rear and left rear of the pallet 10) to photograph. The respective two LIDARs 58 detect objects in front of and behind the pallet 10. According to the LIDARs 58, it is possible to obtain the distance and direction from the pallet 10 of the detection object. The cameras 56 and the LIDARs 58 transmit the acquired information to the automated traveling ECU 64. Instead of the example shown in FIG. 5, only one of the cameras 56 and the LIDARs 58 may be used.

The communication device 60 communicates (transmits and receives) with the communication device 72*c* of a management server 72 (see FIG. 6), which will be described later, via a wireless communication network such as 4G or 5G. The communication device 60 communicates with a mobile terminal 3 (see FIG. 6) described later via the same wireless communication network. The GNSS receiver 62 acquires the position and orientation of the pallet 10 based on signals from GNSS satellites. The GNSS receiver 62 transmits the acquired information to the automated traveling ECU 64.

The automated traveling ECU 64 includes a processor 64*a* and a storage device 64*b*. The storage device 64*b* stores at least one program for automatically traveling the pallet 10. Further, the storage device 64*b* stores map information as a map database. Alternatively, the processor 64*a* may acquire the map information from the map database stored in a storage device 72*b* (see FIG. 6) of the management server 72.

In a typical example of using the pallet 10, the destination is transmitted from the mobile terminal 3 of the user to the automated traveling ECU 64 via the managing server 72. The automated traveling ECU 64 (processor 64*a*) sets a target travel route from the current position of the pallet 10 to the destination and a target vehicle speed (target speed of the pallet 10) based on the position information of the pallet 10 from the GNSS receiver 62 and the map information of the map data base. The processor 64*a* also changes (updates) the set target travel route and target vehicle speed as necessary on the basis of travel state information and position information of the pallet 10 based on the IMU 54 and the GNSS receiver 62, and the information of the objects around the pallet 10 acquired by the cameras 56 and the LIDARs 58.

The automated traveling ECU 64 transmits the latest target travel route and target vehicle speed to the traveling control ECU 66. The traveling control ECU 66 includes a processor 66*a* and a storage device 66*b*. The storage device 66*b* stores various types of information necessary for the control of each electric motor 36 for the automated traveling of the pallet 10. The processor 66*a* generates a control command value (e.g., command value such as rotational speed and rotational direction) of each motor 36 for traveling the pallet 10 to achieve the target traveling route and the target vehicle speed. The processor 66*a* uses the information indicating the traveling state acquired by the IMU54 to generate the control command value.

The traveling control ECU 66 commands the generated control command value of each motor 36 to each motor controller 68. The motor controller 68 includes a drive circuit configured to control electric power supplied from the power supply 52 to the electric motor 36, and is provided for each of the six electric motors 36. Each motor controller 68 controls energization to each electric motor 36 in accordance with the control command value from the traveling control ECU 66.

According to the control by the automated traveling ECU 64 and the traveling control ECU 66 described above, it is possible to autonomously travel the pallet 10 toward the destination.

1-2. Configuration Example of Operation Management System for Pallet

Figure 6:
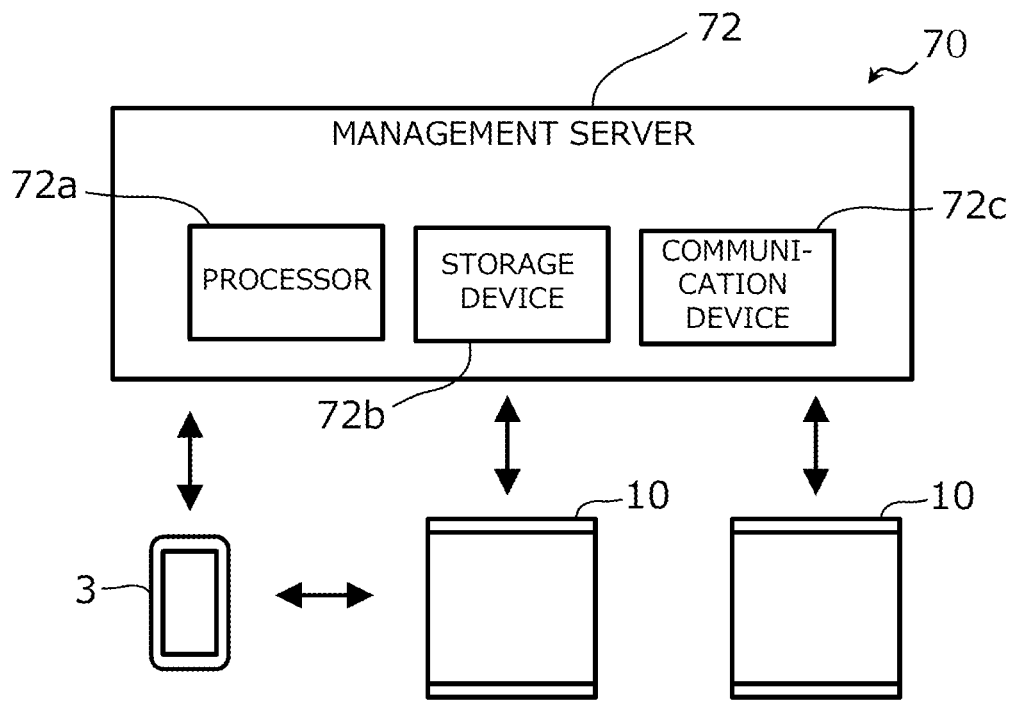
FIG. 6 is a block diagram schematically showing a configuration of an operation management system according to the first embodiment.

FIG. 6 is a block diagram schematically showing a configuration of the operation management system 70 according to the first embodiment. The pallet 10 configured as described above is available in various applications for human movement. One application of such pallet 10 is a mobility service that moves users by performing automated traveling on a road in which a plurality of pallets 10, which are operation-managed, are planned to coexist with pedestrians. An example of a typical mobility service is a transportation service that transports users towards a desired destination.

The above-described mobility service more convenient when it is accompanied by a vehicle dispatch service that dispatches the pallet 10 in response to a request from users. In order to realize the mobility service accompanied by the vehicle dispatch, the operation management system 70 includes a one or plurality of pallets 10, the mobile terminal 3 and the management server 72, as shown in FIG. 6. The mobile terminal 3 is owned by the user of the pallet 10, and is, for example, a smartphone or a tablet PC. The mobile terminal 3 includes a processor, a storage device, and a communication device.

The management server 72 includes a processor 72*a*, a storage device 72*b*, and a communication device 72*c*. The storage device 72*b* stores at least one program for a mobility service including vehicle dispatch. The processor 72*a* reads and executes the program stored in the storage device 72*b*. Accordingly, various functions for providing a mobility service including vehicle dispatch are realized. For example, the management server 72 (communication device 72*c*) communicates with the communication device 60 and the mobile terminal 3 of each pallet 10 via a wireless communication network. The management server 72 manages information of users. Further, the management server 72 performs operation management of the plurality of pallets 10 including the vehicle dispatch service. The operation management of the plurality of pallets 10 by the management server 72 may include, for example, a remote operation of the pallet 10 in an emergency by an operator via the management server 72.

The basic flow of the vehicle dispatch service of the pallet 10 is as follows. That is, when using the vehicle dispatch service, the user transmits vehicle dispatch reservation information to the management server 72 using the mobile terminal 3. The dispatch reservation information includes a desired pickup location (i.e., passenger-boarding location) and a destination. The management server 72 selects an appropriate pallet 10 from one or more pallets 10 around the user, and transmits the vehicle dispatch reservation information to the selected pallet 10. Upon receiving the dispatch reservation information, the pallet 10 generates an operation plan to go to the passenger-boarding location and travels autonomously according to the operation plan. The pallet 10 provides a mobility service (transportation service) that travels autonomously toward the destination after picking up the user at the passenger-boarding location.

In addition, the mobility services with vehicle dispatch may be provided with shared ride services. The mobility services may also be provided without the vehicle dispatch service. Specifically, for example, a user who wishes to ride a vehicle approaches the pallet 10 traveling in the vicinity. Then, the pallet 10 detects the user and stops. The user rides on the pallet 10 after performing a predetermined riding process using the mobile terminal 3. Alternatively, the mobility service may be provided without the use of the management server, using a riding method in which the user goes to a predetermined stop and rides on the pallet 10 waiting there. Furthermore, the mobility service is not limited to an example in which automated traveling is performed toward the destination set by the user, but may also include, for example, the automated traveling along a predetermined route.

1-3. Handrail Disinfection System

Figure 7:
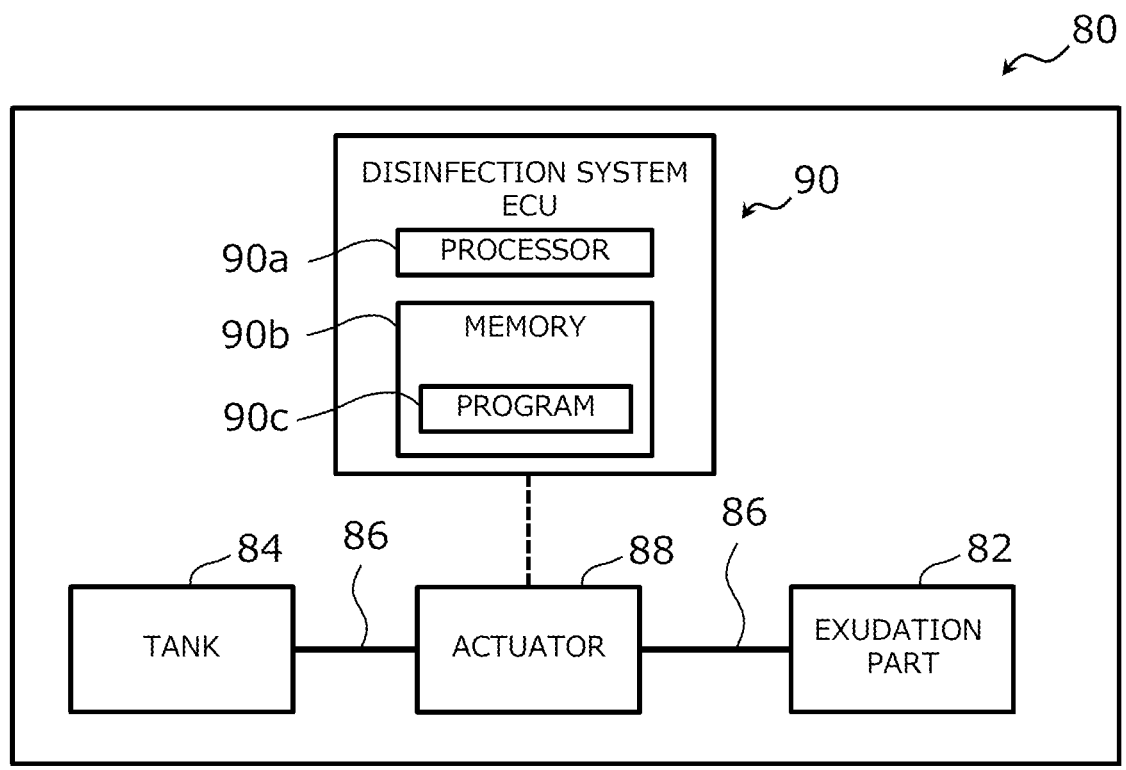
FIG. 7 is a block diagram schematically illustrating an example of a configuration of a handrail disinfection system according to the first embodiment.

FIG. 7 is a block diagram schematically illustrating an example of a configuration of a handrail disinfection system 80 according to the first embodiment. The pallet 10 includes a handrail disinfection system 80 for disinfecting the handrails 22. The handrail disinfection system 80 includes an exudation parts 82, a tank 84, a disinfectant solution piping 86, an actuator 88, and a disinfection system ECU 90.

Figure 8:
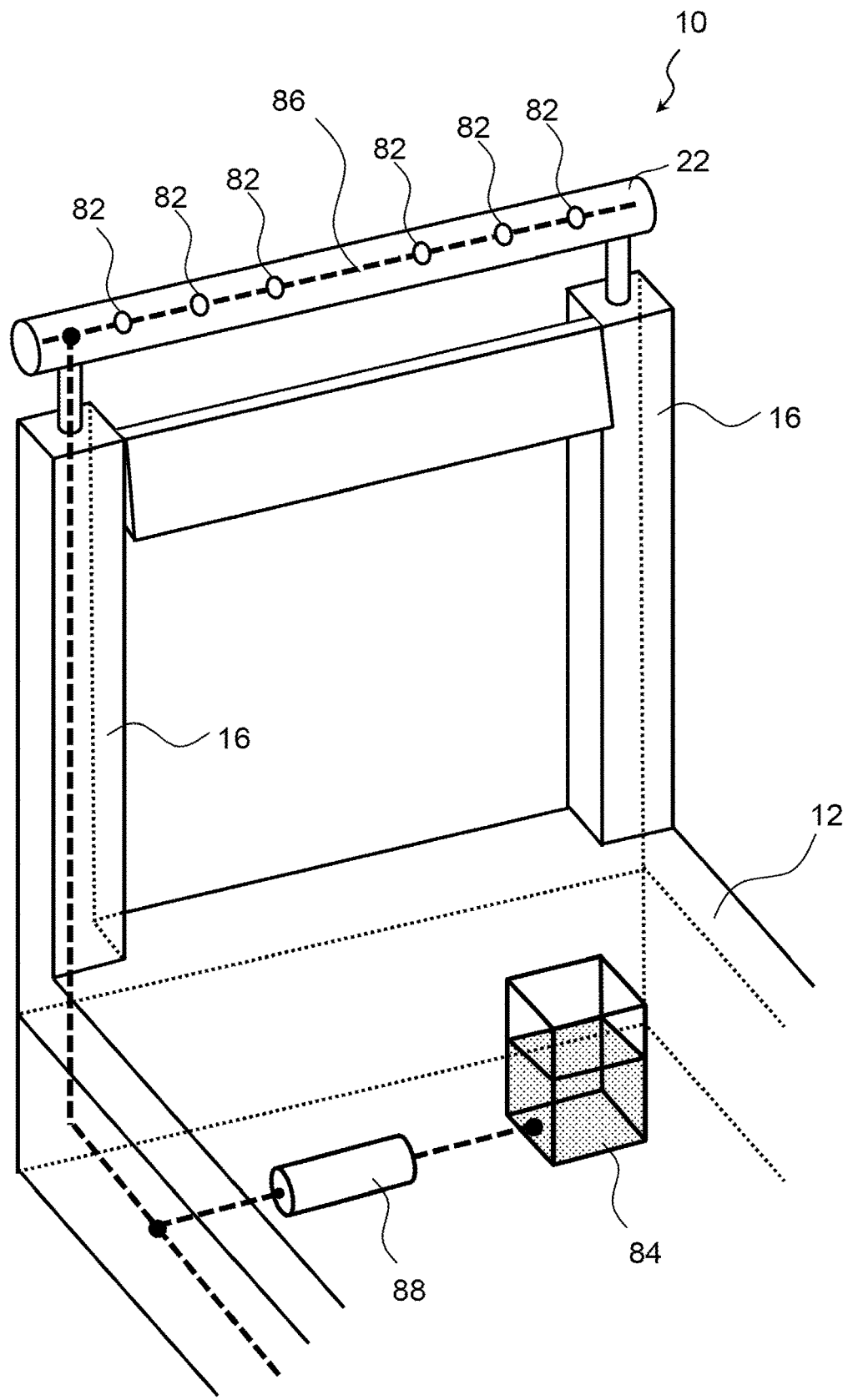
FIG. 8 is a perspective view showing an example of installation of the handrail disinfection system shown in FIG. 7.

FIG. 8 is a perspective view showing an example of installation of the handrail disinfection system 80 shown in FIG. 7. The exudation part 82 is provided on the handrail 22. More specifically, FIG. 8 shows the structure of the handrail 22 disposed at the front end of the pallet 10, but the handrail 22 disposed at the rear end of the pallet 10 has the same structure. The exudation part 82 has one or more exudation holes for exuding the disinfectant solution on the surface of the handrail 22. There is no limitation on the arrangement and number of exudation holes provided in the exudation part 82. In the example shown in FIG. 8, six exudation holes are provided to exude the disinfectant solution throughout the handrail 22.

The tank 84 is for storing the disinfecting solution. As the disinfectant solution used here, a general disinfectant solution having volatility, such as alcohol, sodium hypochlorite, is exemplified. In the example shown in FIG. 8, the tank 84 is disposed between the frame 32 and the top plate 14 as well as the components of the control system 50, such as the power supply 52. Alternatively, the tank 84 may be disposed inside the support 16 if the support 16 has a hollow shape. Alternatively, the tank 84 may be mounted exposed on the top plate 14. By exposing the tank 84, the user (occupant) can easily check the remaining amount of the disinfectant solution. In addition, if a colored disinfectant solution is used, users can also enjoy looking at the color of the disinfectant solution stored in the tank 84.

The tank 84 and the exudation part 82 are connected by the disinfectant solution piping 86. In the example shown in FIG. 8, the disinfectant solution piping 86 is connected to the tank 84 at one end, branches in the middle, passes through the inside of the front and rear supports 16, and is connected to each of the exudation holes of the exudation part 82 provided in the front and rear handrails 22. The actuator 88 is provided in the middle of the disinfectant solution piping 86. The actuator 88 is for pumping the disinfectant solution in the tank 84 to the exudation part 82. An electric pump is exemplified as the actuator 88. In the example shown in FIG. 8, the actuator 88 is disposed between the branch portion of the disinfectant solution piping 86 and the tank 84.

The disinfection system ECU 90 includes a memory 90b including at least one program 90c and a processor 90a coupled to the memory 90b. The number of the memory 90b may be multiple. Also, the number of the processor 90a may be multiple. The processor 90a is configured to control the actuator 88 of the handrail disinfection system 80 by executing the program 90c. In other words, the disinfection system ECU 90 functions as a controller of the handrail disinfection system 80 according to the present embodiment. The disinfection system ECU 90 is supplied with electric power from the power supply 52.

1-4. Operation of Handrail Disinfection System

The handrail disinfection system 80 according to the present embodiment performs a disinfecting process for controlling the actuator 88 to exude the disinfectant solution from the exudation part 82 to the surface of the handrails 22 when a predetermined execution condition is satisfied. The execution condition in the handrail disinfection system according to the present embodiment is whether the elapsed time from the execution of the previous disinfecting process has exceeded a predetermined time. Hereinafter, the disinfecting process performed by the handrail disinfection system according to the present embodiment will be described with reference to FIG. 9.

Figure 9:
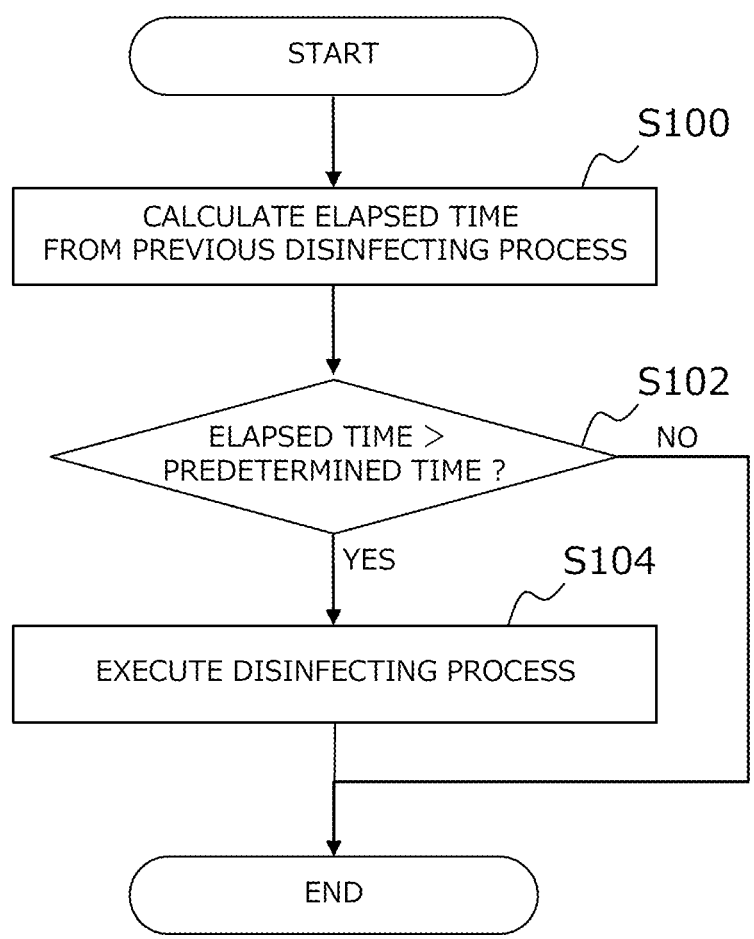
FIG. 9 is a flowchart illustrating a control routine implemented in a handrail disinfection system according to the first embodiment.

FIG. 9 is a flowchart illustrating a control routine implemented in a handrail disinfection system according to the first embodiment. The control routine shown in FIG. 9 is repeatedly executed at a predetermined control cycle during the mobility service of the pallet 10, for example.

First, in step S100, the disinfection system ECU 90 calculates the elapsed time from the previous disinfecting process. When the disinfecting process has not been executed yet, the elapsed time from the opening instruction of the first control routine is calculated. When the elapsed time is calculated, the process proceeds to the next step S102.

In step S102, the disinfection system ECU 90 determines whether the elapsed time calculated in step S100 exceeds a predetermined time. As the predetermined time, a predetermined time (e.g., several minutes) is used in consideration of a required time between destinations where occupants get on and off. As a result of the determination, when the elapsed time has not reached the predetermined time, the present routine is terminated, and when the elapsed time has reached the predetermined time, the routine proceeds to the next step S104.

In step S104, the disinfection system ECU 90 executes the disinfecting process. Here, the disinfection system ECU 90 drives the actuator 88 to cause the disinfectant solution in the tank 84 to be exuded from the exudation part 82. The exuded disinfectant solution penetrates and adheres to the surface of the handrail 22

According to the control as described above, the handrail 22 is periodically disinfected with the disinfectant solution. This makes it possible to disinfect the handrail automatically without any particular effort.

1-5. Modified Examples

The handrail disinfection system of the first embodiment may be modified as follows.

The handrail 22 included in the pallet 10 is not limited. That is, the handrail 22 is not limited to its shape, arrangement, number as long as it is for the users in the pallet 10 to grasp. For example, the handrail 22 may be provided around the table 20, or may be provided along the vertical direction of one or more of the supports 16. It should be noted that this modification can be similarly applied to the handrail disinfection system of another embodiment described later.

2. Second Embodiment

2-1. Features of Second Embodiment

It is efficient to disinfect the handrail 22 immediately after the user who was holding the handrail 22 gets off the vehicle. Therefore, the handrail disinfection system 100 of the second embodiment has a feature in that whether the user of the pallet 10 gets off is adopted as the execution condition for the disinfecting process.

2-2. Handrail Disinfection System of Second Embodiment

Figure 10:
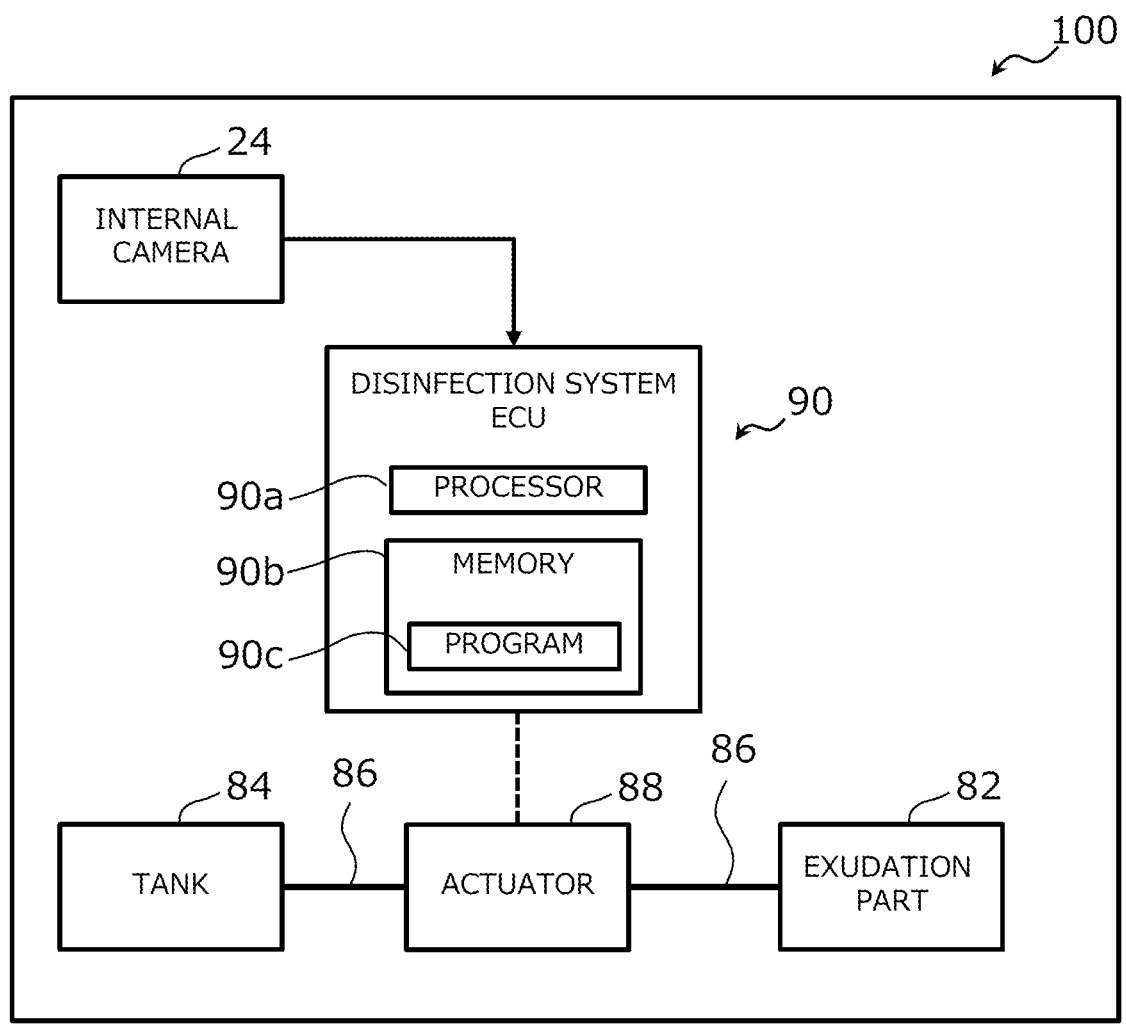
FIG. 10 is a block diagram schematically illustrating an example of the configuration of a handrail disinfection system according to a second embodiment.

FIG. 10 is a block diagram schematically illustrating an example of the configuration of the handrail disinfection system 100 according to the second embodiment. In addition to the configuration similar to that of the handrail disinfection system 80 of the first embodiment, the handrail disinfection system 100 of the second embodiment further includes one or more internal cameras 24.

The one or more internal cameras 24 are examples of internal monitoring sensors for monitoring the condition of the user 2 riding on the riding floor 12. The one or more internal cameras 24 is provided on the inward of each support 16 so as to capture the user riding on the riding floor 12 of the pallet 10 from the right front, left front, right rear, and left rear. The image information captured by the internal cameras 24 is stored as occupant information in the memory 90*b* of the disinfection system ECU 90.

The program 90*c* stored in the memory 90*b* includes a program for performing a getting-off determination process. The getting-off determination process is a process for determining whether the occupant of the pallet 10 has got off from the riding floor 12 based on the occupant information obtained from the internal monitoring sensors. The processor 90*a* executes the program 90*c* to perform the getting-off determination process, and controls the actuator 88 of the handrail disinfection system 100 based on the result.

2-3. Operation of Handrail Disinfection System of Second Embodiment

The handrail disinfection system 100 according to the second embodiment performs the disinfecting process when a predetermined execution condition is satisfied. The execution condition in the handrail disinfection system according to the second embodiment is whether the occupant of the pallet 10 has got off. Hereinafter, the disinfecting process performed by the handrail disinfection system according to the present embodiment will be described with reference to FIG. 11.

Figure 11:
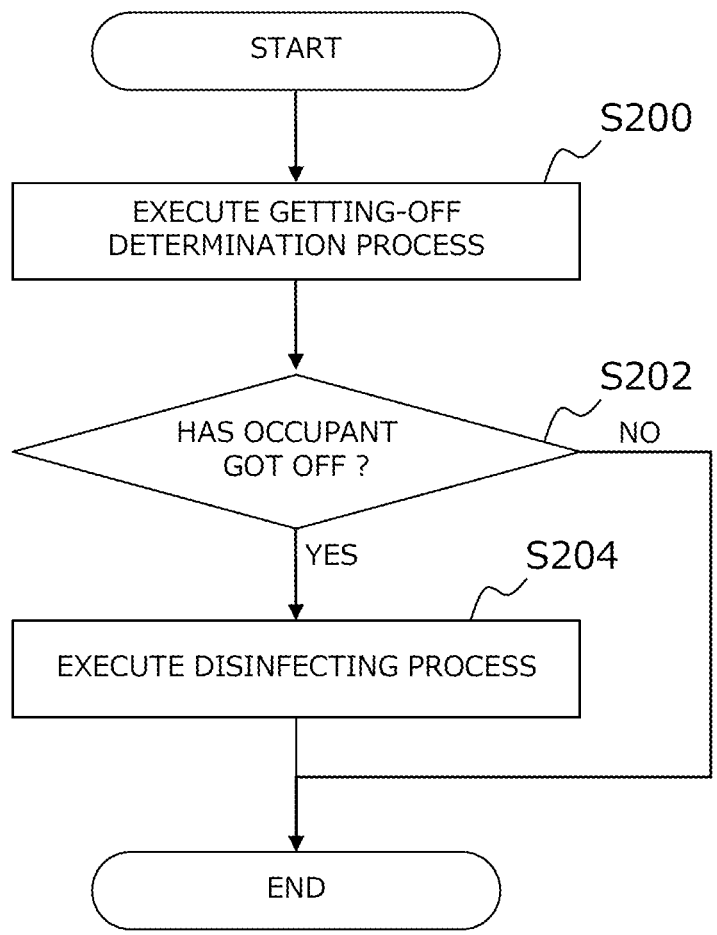
FIG. 11 is a flowchart illustrating a control routine implemented in the handrail disinfection system according to the second embodiment.

FIG. 11 is a flowchart illustrating a control routine implemented in the handrail disinfection system according to the second embodiment. The control routine shown in FIG. 11 is repeatedly executed at a predetermined control cycle during the mobility service of the pallet 10, for example.

First, in step S200, the disinfection system ECU 90 performs the getting-off determination process. Here, the disinfection system ECU 90 reads out the image information captured by the inner cameras 24 from the memory 90*b*. Then, based on the read image information, it is determined whether the occupant has got off.

In the next step S202, the disinfection system ECU 90 determines whether the getting-off of the occupant is determined in the getting-off determination process of step S200. As a result, the routine is terminated when the getting-off of the occupant is not determined, and the routine processes to step S204 when the getting-off of the occupant is determined.

In step S204, the disinfection system ECU 90 performs the disinfecting process. Here, the same process as the above-described step S104 is performed.

According to the control as described above, the handrail 22 is disinfected by the disinfectant solution at the timing when the occupant has got off. This makes it possible to perform disinfecting efficiently immediately after the occupant gets off the vehicle without any special labor.

2-4. Modified Examples

The handrail disinfection system of the second embodiment may be modified as follows.

The getting-off determination process may be configured to use the internal monitoring sensors different from the internal cameras 24. Such internal monitoring sensors include, for example, a load sensor to detect a load applied to the riding floor 12. Load information detected by the load sensor is stored in the memory 90*b* as occupant information. In the getting-off determination process using the load sensor, the disinfection system ECU 90 reads the load information detected by the load sensor from the memory 90*b*. Then, when the change in the load included in the read load information includes a decrease in the weight of the person, the disinfection system ECU 90 may determine that the occupant has got off.

3. Third Embodiment

3-1. Features of Third Embodiment

Figure 12:
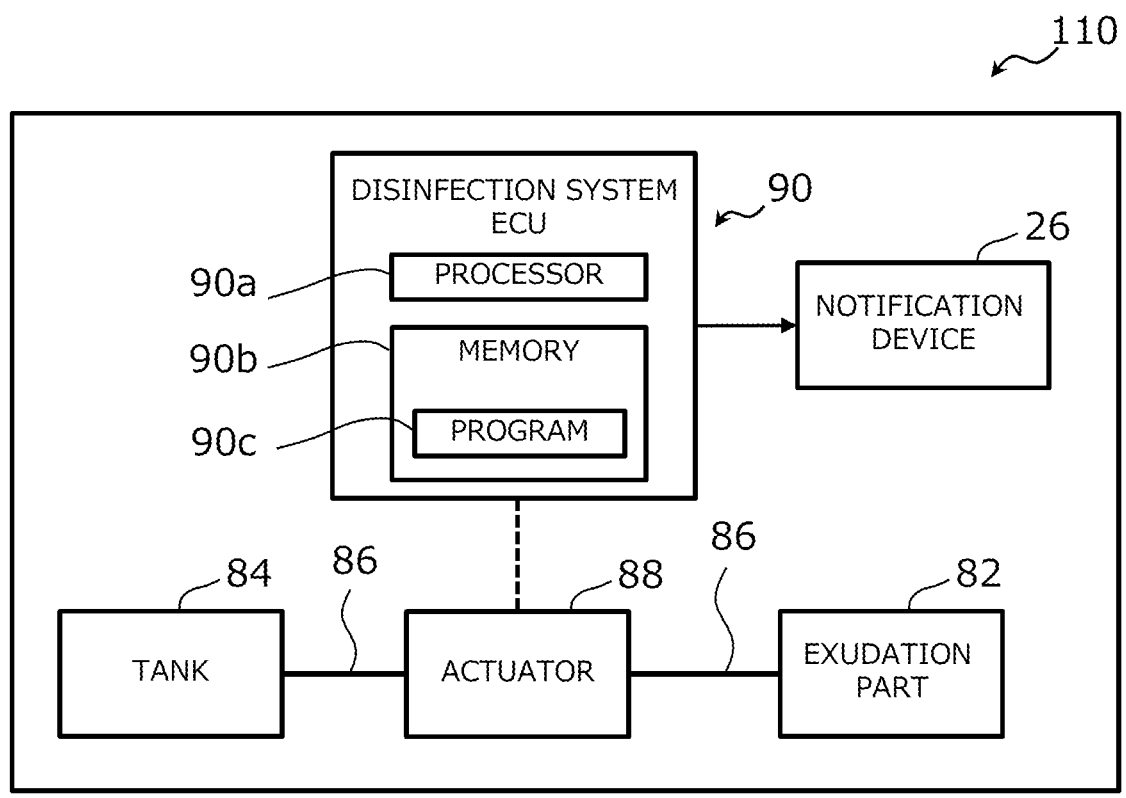
FIG. 12 is a block diagram schematically illustrating an example of a configuration of a handrail disinfection system according to a third embodiment.

A handrail disinfection system 110 of the third embodiment has a feature in that it performs a notification process to notify occupants of the execution status of the disinfecting process. FIG. 12 is a block diagram schematically illustrating an example of a configuration of a handrail disinfection system 110 according to the third embodiment. In addition to the configuration similar to that of the handrail disinfection system 80 of the first embodiment, the handrail disinfection system 110 of the third embodiment includes a notification device 26. The notification device 26 is an output device for notifying the occupant. For example, the notification device 26 is a display for performing notification by display. Alternatively, the notification device 26 is a speaker for voice notification.

The program 90c stored in the memory 90b includes a program for performing the notification process. In the notification process, specifically, the disinfection system ECU 90 notifies the occupant that the handrail 22 have been disinfected when the disinfecting process is completed. Alternatively, the disinfection system ECU 90 notifies the occupant that the handrail 22 is being disinfected during the execution of the disinfecting process. According to such a notification process, the occupant who newly rides on the pallet 10 can know that the handrail 22 has been disinfected, so that the occupant can grasp the handrail 22 with peace of mind. In addition, during the execution of the disinfecting process, since the occupant can know that the handrail 22 is being disinfected, the occupant can take measures such as releasing the hand holding the handrail 22 temporarily.

4. Fourth Embodiment

4-1. Features of Fourth Embodiment

The disinfecting process of the handrail 22 is economically and efficiently performed by focusing down the area of the handrail 22 actually grasped by the occupants. Therefore, a handrail disinfection system 120 of the fourth embodiment is characterized in that it allows individual disinfection for each of a plurality of areas when disinfecting the handrail 22 provided in the pallet 10. More specifically, the handrail disinfection system 120 performs a disinfection area determination process for determining a disinfection area to be disinfected among the respective areas when the handrail 22 is compartmentalized into a plurality of areas.

In the disinfection area determination process, the handrail disinfection system 120 performs an area-specific getting-off determination process to determine, for example, whether the occupant of the pallet 10 has got off, for each riding area of the riding floor 12. Then, the handrail disinfection system 120 performs the disinfecting process limited to the disinfecting area by using the area of the handrail 22 corresponding to the riding area in which the occupant who has left the vehicle is riding as the disinfection area.

4-2. Handrail Disinfection System of Fourth Embodiment

Figure 13:
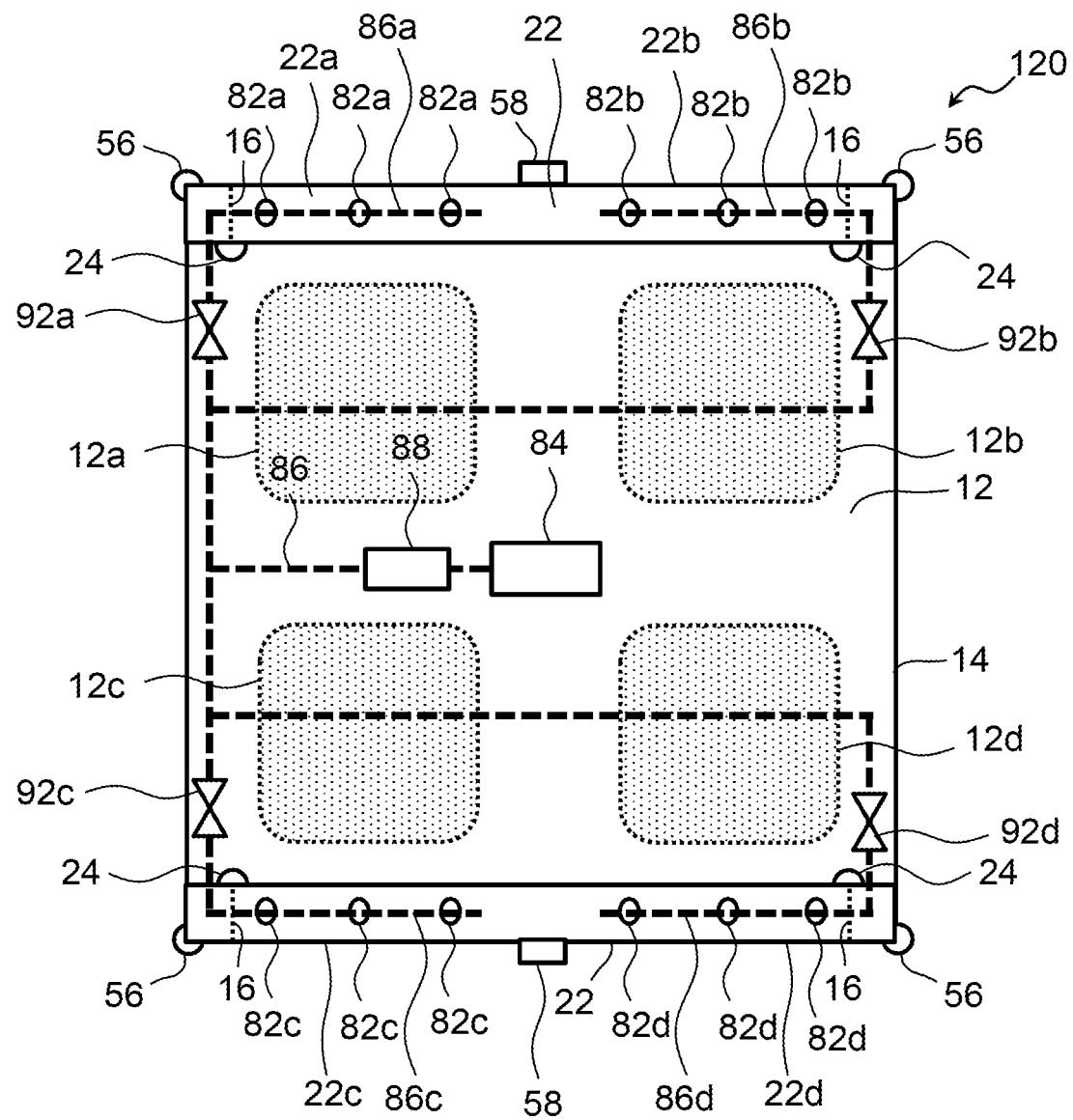
FIG. 13 is a diagram schematically showing an installation example of a handrail disinfection system mounted on the stand-up type vehicle according to a fourth embodiment.
Figure 14:
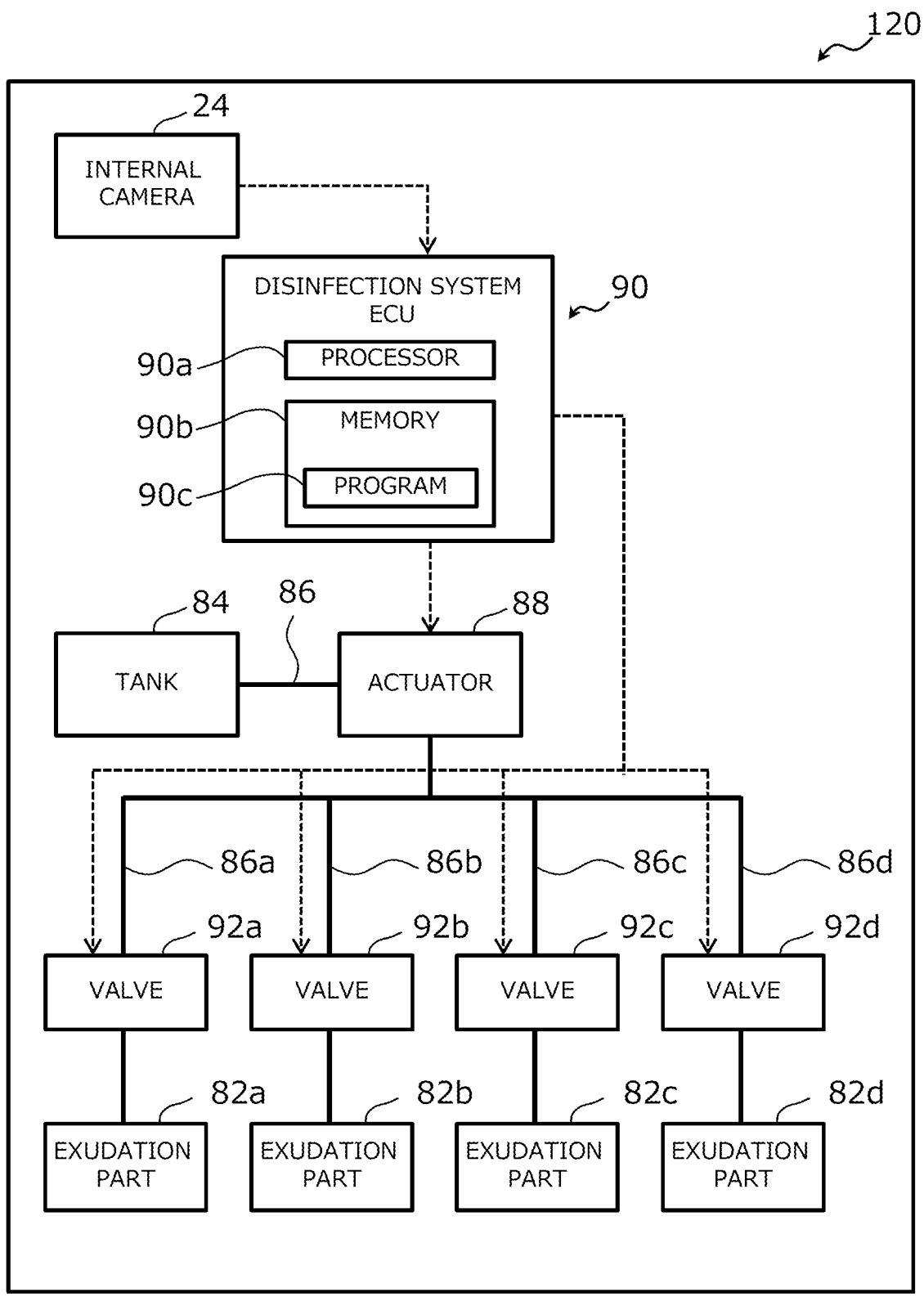
FIG. 14 is a block diagram schematically illustrating an example of a configuration of a handrail disinfection system according to the fourth embodiment.

FIG. 13 is a diagram schematically showing an installation example of a handrail disinfection system mounted on a stand-up type vehicle according to the fourth embodiment. Further, FIG. 14 is a block diagram schematically illustrating an example of the configuration of the handrail disinfection system according to the fourth embodiment. The handrail 22 of the pallet 10 according to the fourth embodiment includes a handrail 22a held by an occupant riding in the left front riding area 12a, a handrail 22b held by an occupant riding in the right front riding area 12b, a handrail 22c held by an occupant riding in the left rear riding area 12c, and a handrail 22d held by an occupant riding in the left rear riding area 12d. That is, the riding areas 12a, 12b, 12c, and 12d correspond to the handrails 22a, 22b, 22c, and 22d, respectively. The handrails 22a, 22b, 22c, and 22d may be formed integrally with adjacent handrails, that is, the handrails 22a and 22b or the handrails 22c and 22d, or may be attached independently of each other.

Each exudation part 82a, 82b, 82c, and 82d included in the exudation part 82 is provided in each of the handrail 22a, 22b, 22c, and 22d. The configuration of the exudation parts 82a, 82b, 82c, and 82d is the same as that of the exudation part 82 in the handrail disinfection system 80 of the first embodiment.

The tank 84 and the exudation parts 82a, 82b, 82c, and 82d are connected by the disinfectant solution piping 86. In the example shown in FIG. 13, one end of the disinfection solution piping 86 is connected to the tank 84, and branches into the disinfectant solution piping 86a, 86b, 86c, and 86d in the middle. The disinfectant solution piping 86a, 86b, 86c, and 86d after branching is connected to each of the exudation parts 82a, 82b, 82c, and 82d through the inside of the front and rear left and right supports 16, respectively. The actuator 88 is provided in the middle of the disinfectant solution piping 86 before branching. Each of opening-closing valves 92a, 92b, 92c, and 92d is connected to each of the exudation parts 82a, 82b, 82c, and 82d.

The handrail disinfection system 120 includes one or a plurality of internal cameras 24 as the internal monitoring sensors for monitoring the state of the occupant 2 riding on the riding floor 12. The image information captured by the internal cameras 24 is stored as occupant information in the memory 90b of the disinfection system ECU 90.

The program 90c stored in the memory 90b includes a program for performing the disinfection area determination process and the disinfecting process limited to the disinfection area. The processor 90a executes the disinfection area determination process by executing the program 90c, and performs disinfecting process limited to the disinfection area based on the determination result.

4-3. Operation of Handrail Disinfection System of Fourth Embodiment

The handrail disinfection system 120 according to the fourth embodiment performs disinfecting process when a predetermined execution condition is satisfied. The execution condition in the handrail disinfection system according to the fourth embodiment is whether the occupant riding in any of the riding areas 12a, 12b, 12c, and 12d of the riding floor 12 of the pallet 10 has got off. Hereinafter, the disinfecting process performed by the handrail disinfection system according to the present embodiment will be described with reference to FIG. 15.

Figure 15:
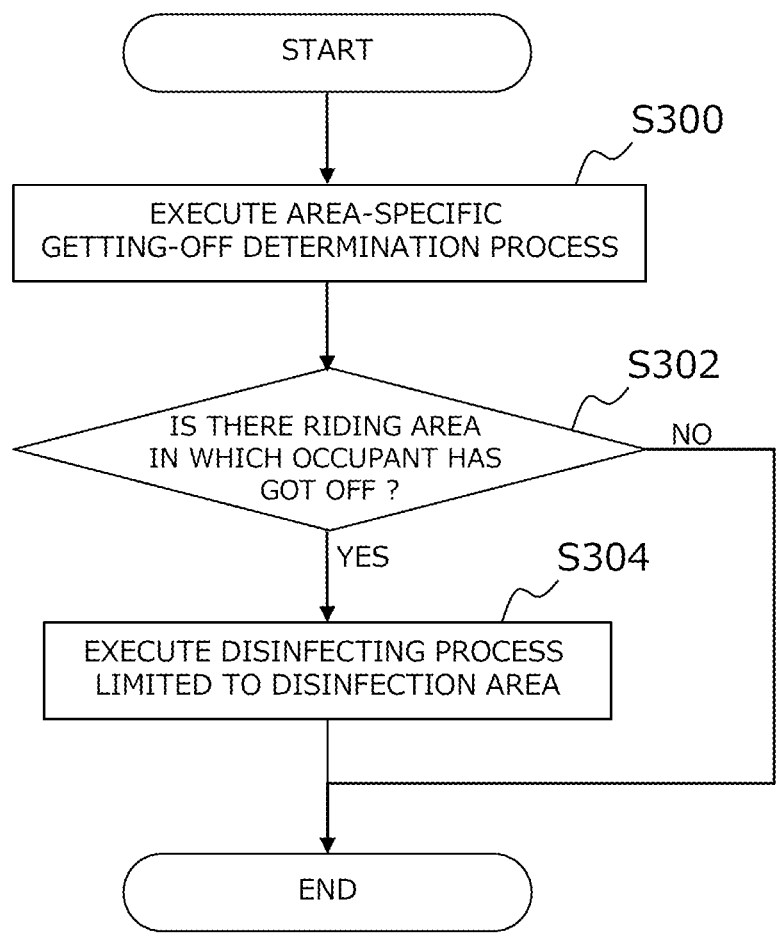
FIG. 15 is a flowchart illustrating a control routine implemented in the handrail disinfection system according to the fourth embodiment.

FIG. 15 is a flowchart illustrating a control routine implemented in the handrail disinfection system according to the fourth embodiment. The control routine shown in FIG. 15 is repeatedly executed at a predetermined control cycle during the mobility service of the pallet 10, for example.

In step S300 and step S302, the disinfection system ECU 90 performs the disinfection area determination process. First, in step S300, the disinfection system ECU 90 reads out the image information captured by the internal cameras 24 from the memory 90b. Then, based on the read image information, for each area of the riding areas 12a, 12b, 12c, and 12d, it is determined whether the occupant has got off.

In the next step S302, the disinfection system ECU 90 determines whether there is a riding area in which the occupant has got off in the area-specific getting-off determination process of step S300. As a result, when it is determined that the occupant has not got off in any of the riding areas, it is determined that there is no disinfection area, and the present routine is terminated. On the other hand, when it is determined that the occupant has got off in any of the riding areas, it is determined that the area of the handrail 22 corresponding to the riding area in which the riding is determined to get off is the disinfection area, and the process proceeds to step S304.

In step S304, the disinfection system ECU 90 executes the disinfecting process limited to the disinfection area. Here, the disinfection system ECU 90 opens the opening-closing valve corresponding to the disinfection area in which the getting-off is determined, and closes the opening and closing valve corresponding to the area in which the getting-off is not determined. Then, the disinfection system ECU 90 drives the actuator 88 to cause the disinfectant solution in the tanks 84 to be exuded from the exudation part corresponding to the area where the occupant has been got off.

According to the control as described above, the handrail 22 corresponding to the area where the occupant has got off is disinfected by the disinfectant solution. This makes it possible to disinfect the vehicle economically and efficiently, limited to the area where the occupant has got off.

4-4. Modified Examples

The handrail disinfection system of the fourth embodiment may be modified as follows.

The area-specific getting-off determination process may be configured to use the internal monitoring sensors different from the internal cameras 24. Such internal monitoring sensors include, for example, load sensors to detect the load applied to each area of the riding areas 12a, 12b, 12c, and 12d. The load information of each area detected by the load sensors is stored in the memory 90b as the occupant information. In the disinfection area determination process using the load sensor, the disinfection system ECU 90 reads out the load information detected by the load sensors corresponding to the respective areas from the memory 90b. Then, when the change in the load included in the read load information includes a decrease in the weight of the person, the disinfection system ECU 90 may determine that the occupant has got off the vehicle in the corresponding area, and may determine that the area is the disinfection area.

Alternatively, in the area-specific getting-off determination process, contact sensors for detecting that the occupant is grasping the handrail 22 may be used as the internal monitoring sensors. In this case, the contact sensors are provided in each area of the handrails 22a, 22b, 22c, and 22d. Contact information of each area detected by the contact sensors is stored in the memory 90b as the occupant information. In the disinfection area determination process using the contact sensors, the disinfection system ECU 90 reads out the contact information detected by the contact sensors corresponding to the respective areas from the memory 90b. Next, when it is determined that a predetermined time has elapsed after the occupant leaves the handrail 22 based on the read contact information, the disinfection system ECU 90 may determine that the area is a disinfection area as the occupant gets off in the corresponding area.

Alternatively, when the pallet 10 has a plurality of gateways, it may be used human detection sensors provided in a plurality of gateways as the internal monitoring sensors. Getting-off information of each gateway detected by the human sensors is stored in the memory 90b as the occupant information. Each of the plurality of gateways corresponds to each area of the handrails 22a, 22b, 22c, and 22d. For example, the gateway on the left side of the pallet 10 corresponds to the handrails 22a and 22c, and the gateway on the right side of the pallet 10 corresponds to the handrails 22b and 22d. In the disinfection area determination process using the human sensor, the disinfection system ECU 90 reads out the getting-off information detected by the human sensor from the memory 90b. Then, the disinfection system ECU 90 may determine the area corresponding to the gateway where the occupant has got off the vehicle as the disinfection area based on the read getting-off information.

The form of division of a plurality of areas of one or a more handrails 22 is not limited. In other words, the plurality of areas may be further finely compartmentalized than the 4 areas described above as long as the disinfectant solution can be individually exuded from the disinfectant exudation part of each area.

Various known forms may be employed for the configuration in which the disinfectant solution is exuded from the exudation parts 82a, 82b, 82c, and 82d of each area of the handrails 22a, 22b, 22c, and 22d. For example, the actuator 88 may not be disposed in the middle of the disinfectant solution piping 86 before branching, and each of the actuators (electric pumps) may be individually disposed in the disinfectant solution piping 86a, 86b, 86c, and 86d.

5. Fifth Embodiment 5-1. Features of Fifth Embodiment

Figure 16:
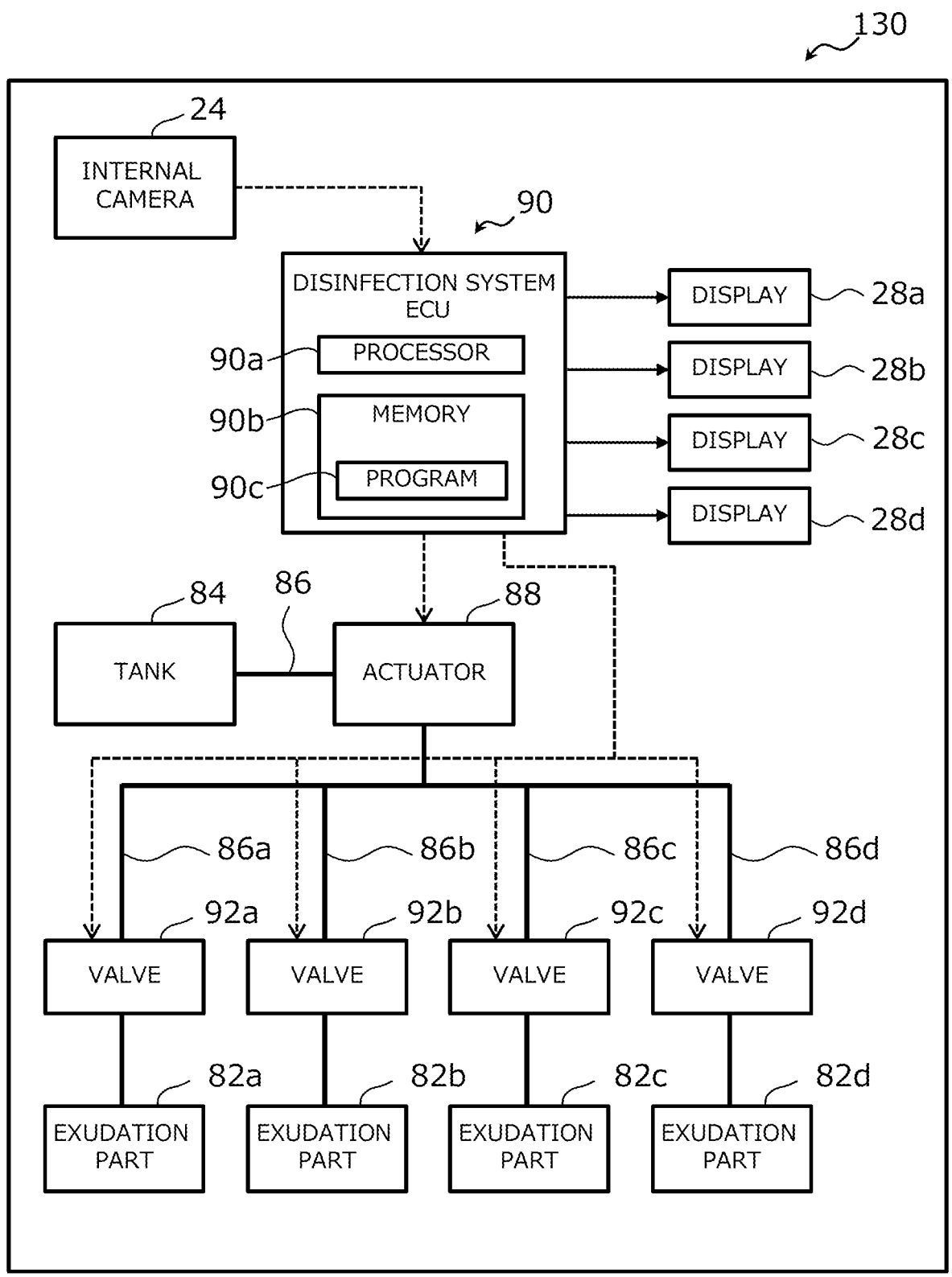
FIG. 16 is a block diagram schematically illustrating an example of a configuration of a handrail disinfection system according to a fifth embodiment.
Figure 17:
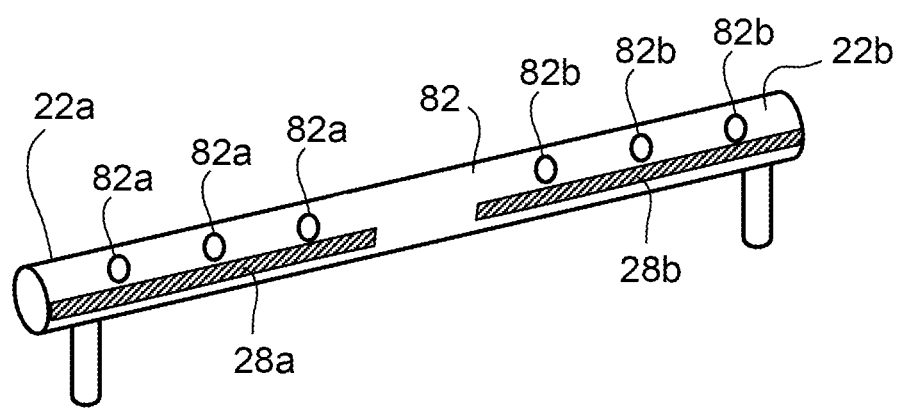
FIG. 17 is a diagram illustrating an example of displays provided in the handrail disinfection system according to the fifth embodiment.

A handrail disinfection system 130 according to the fifth embodiment is characterized in that it performs a display process to clearly indicate to the occupants the execution status of the disinfecting process among by area among the handrails 22. FIG. 16 is a block diagram schematically illustrating an example of the configuration of the handrail disinfection system 130 according to the fifth embodiment. In addition to the configuration similar to that of the handrail disinfection system 120 of the fourth embodiment, the handrail disinfection system 130 of the fifth embodiment includes a displays 28a, 28b, 28c, and 28d associated with the handrails 22a, 22b, 22c, and 22d, respectively. The displays 28a, 28b, 28c, and 28d are displays for clearly indicating the disinfection situation of the handrail 22 to the occupant by area. FIG. 17 is a diagram illustrating an example of displays provided in the handrail disinfection system according to the fifth embodiment. As shown in FIG. 17, the handrails 22a, 22b in front of the pallet 10 are provided with the displays 28a, 28b, respectively, which extend in the width direction of the pallet 10. Incidentally, the handrails 22a, 22b in front of the pallet 10 are shown in FIG. 17, the handrail 22c, 22d behind the pallet 10 are similarly provided with the displays 28c, 28d, respectively, extending in the width direction of the pallet 10. Each of the displays 28a, 28b, 28c, and 28d is an illumination lamp such as LEDs disposed along the width direction of the pallet 10, for example.

The program 90c stored in the memory 90b includes a program for performing the display process. In the display process, specifically, the disinfection system ECU 90 turns on the displays as a display indicating that the disinfection area determined by the disinfection area determination process has not been disinfected. In addition, the disinfection system ECU 90 switches the display from the lit-state display to the unlit-state display in response to completion of the disinfecting process. According to such a display process, the occupant who rides on the pallet 10 can know whether the handrail 22 has been disinfected by area, so that the occupant can select and grasp the area of the disinfected handrail 22.

5-2. Modified Examples

The handrail disinfection system of the fifth embodiment may be modified as follows.

The displays 28a, 28b, 28c, and 28d are not limited to the length and arrangement of the LEDs as long as they can clearly indicate to the occupant that the area of the corresponding handrail 22 has been disinfected. For example, each of the displays 28a, 28b, 28c, and 28d may be a small liquid crystal display installed in each of the handrails 22a, 22b, 22c, and 22d.

6. Sixth Embodiment

6-1. Features of Sixth Embodiment

When the disinfecting process is performed in the pallet 10 during traveling, the faster the vehicle speed, the easier the disinfectant solution tends to be vaporized. In addition, in the case of providing the vehicle dispatch service by the pallet 10, it is desirable to complete the disinfecting process before arriving at the pickup place.

Therefore, the handrail disinfection system according to the sixth embodiment is characterized in that the amount of disinfectant solution in the disinfecting process is adjusted in accordance with a set vehicle speed or a required time to the next pickup place of the pallet 10. More specifically, the memory 90b stores the set vehicle speed in the section up to the next pickup place determined based on the operation plan of the pallet 10. The program 90c stored in the memory 90b includes a program for adjusting the exudation amount of the disinfectant according to the set vehicle speed in the disinfecting process. In the disinfecting process, specifically, the disinfection system ECU 90 executes programs to control the actuator 88 so that the amount of the disinfectant solution exuded larges as the set vehicle speed increases.

Alternatively, the memory 90b stores the required time to the next pickup place determined based on the operation plan of the pallet 10. The program 90c stored in the memory 90b includes a program for adjusting the exudation amount of the disinfectant solution in accordance with the required time in the disinfecting process. In the disinfecting process, specifically, the disinfection system ECU 90 executes programs to control the actuator 88 so that the amount of the disinfectant solution exuded reduces as the required time is shorter.

According to the handrail disinfection system of the sixth embodiment described above, since the amount of exudation of the disinfectant solution can be adjusted according to the set vehicle speed of the pallet 10, it is possible to reliably disinfect the handrails 22 even in an environment in which the disinfectant solution is easily vaporized. In addition, since the amount of exudation of the disinfectant solution can be adjusted according to the required time to the pickup place of the pallet 10, disinfection can be reliably completed by the time of riding of the user.

What is claimed is:

1. A handrail disinfection system for vehicle with handrail, the system comprising:
   a tank to store disinfectant solution;
   an exudation part provided on the handrail;
   one or more sensors to detect a state of an occupant riding in the vehicle;
   an actuator for exuding the disinfectant solution stored in the tank from the exudation part; and
   a controller for controlling the actuator,
   wherein the controller comprises:
      at least one memory including at least one program; and
      at least one processor coupled with the at least one memory, and
   wherein the at least one processor executes upon execution of the at least one program,
   performing a disinfecting process in which the actuator is controlled to exude the disinfectant solution from the exudation part to a surface of the handrail when a predetermined execution condition is satisfied;
   wherein the at least one memory is configured to store occupant information detected by the one or more sensors,
   wherein the at least one processor is configured to execute, by executing the at least one program, a getting-off determination process to determine whether the occupant has got off, based on the occupant information,
   wherein the execution condition is a condition that is satisfied when getting-off of the occupant is determined in the getting-off determination process,
   wherein the at least one memory stores a set vehicle speed to a next pickup location determined based on an operation plan of the vehicle, and
   wherein the at least one processor is configured to increase, by executing the at least one program, amount of disinfectant solution exuded from the disinfection part as the set vehicle speed increases in the disinfecting process.

2. The handrail disinfection system for vehicle with handrail according to claim 1, wherein the execution condition is a condition that is satisfied when an elapsed time since a previous execution of the disinfecting process exceeds a predetermined time.

3. The handrail disinfection system for vehicle with handrail according to claim 1,
   wherein, when the handrail is divided into a plurality of areas, the disinfection exudation part is provided in each of the plurality of areas,
   wherein the actuator is configured to be capable of exuding the disinfectant solution in each area of the plurality of areas, and
   wherein the at least one processor executes upon execution of the at least one program:
      executing a disinfection area determination process for determining a disinfection area to be disinfected among the plurality of areas of the handrail based on the occupant information; and
      executing the disinfecting process by limiting the disinfection area determination process to the disinfection area determined by the disinfection area determination process.

4. The handrail disinfection system for vehicle with handrail according to in claim 3, wherein the disinfection area determination process is configured to determine whether the occupant has got off for each riding area of a riding floor on the basis of the occupant information, and determine an area of the handrail corresponding to a riding area in which the occupant has got off as the disinfection area.

5. The handrail disinfection system for vehicle with handrail according to claim 3, wherein the disinfection area determination process is configured to determine an area grasped by the occupant among the plurality of areas as the disinfection area based on the occupant information.

6. The handrail disinfection system for vehicle with handrail according to claim 3, wherein the vehicle has a plurality of gateways for occupants to get on and off, and
wherein the disinfection area determination process is configured to determine the gateways where the occupant has got off from among the plurality of gateways, based on the occupant information, and determine an area corresponding to the gateway where the occupant has got off as the disinfection area.

7. The handrail disinfection system for vehicle with handrails according to claim 3, further comprising a plurality of displays provided in association with each of the plurality of areas,
wherein the plurality of displays are configured to be capable of independently displaying a disinfection state of a corresponding one of the plurality of areas, and
wherein the at least one processor is configured to, by executing the at least one program, display on a corresponding display among the plurality of the display a display indicating that the disinfection area determined by the disinfection area determination process is before disinfection, and to switch to a display indicating that the disinfecting process for the disinfection area has been completed in response to completion of the disinfecting process.

8. The handrail disinfection system for vehicle with handrail according to claim 7,
wherein the plurality of displays includes an illumination lamp provided along each of the plurality of areas, and
wherein in the illumination lamp, a display indicating that the disinfecting process has not been completed corresponds to lit-state, and a display indicating that the disinfecting process has been completed corresponds to unlit-state.

9. The handrail disinfection system for vehicle with handrail according to claim 1, wherein the at least one processor is configured to execute, by executing the at least one program, a notification process for notifying occupants when the disinfecting process is executed.

10. A handrail disinfection system for vehicle with handrail, the system comprising:
a tank to store disinfectant solution;
an exudation part provided on the handrail;
one or more sensors to detect a state of an occupant riding in the vehicle;
an actuator for exuding the disinfectant solution stored in the tank from the exudation part; and
a controller for controlling the actuator,
wherein the controller comprises:
at least one memory including at least one program; and
at least one processor coupled with the at least one memory, and
wherein the at least one processor executes upon execution of the at least one program,
performing a disinfecting process in which the actuator is controlled to exude the disinfectant solution from the exudation part to a surface of the handrail when a predetermined execution condition is satisfied,
wherein the at least one memory is configured to store occupant information detected by the one or more sensors,
wherein the at least one processor is configured to execute, by executing the at least one program, a getting-off determination process to determine whether the occupant has got off, based on the occupant information,
wherein the execution condition that is satisfied when getting-off of the occupant is determined in the getting-off determination process,
wherein the at least one memory stores a time to arrive at a next pickup location determined based on an operation plan of the vehicle, and
wherein the at least one processor is configured to reduce, by executing the at least one program, amount of the disinfectant solution exuded from the exudation part in the disinfecting process as the time required is shorter.

* * * * *